(12) United States Patent
Fischvogt

(10) Patent No.: US 8,603,107 B2
(45) Date of Patent: Dec. 10, 2013

(54) TISSUE ANCHOR APPLICATOR

(75) Inventor: Gregory Fischvogt, Hamden, CT (US)

(73) Assignee: Covidien LP, Mansfield, MA (US)

( * ) Notice: Subject to any disclaimer, the term of this patent is extended or adjusted under 35 U.S.C. 154(b) by 432 days.

(21) Appl. No.: 12/896,936

(22) Filed: Oct. 4, 2010

(65) Prior Publication Data

US 2011/0087281 A1   Apr. 14, 2011

Related U.S. Application Data

(60) Provisional application No. 61/250,070, filed on Oct. 9, 2009.

(51) Int. Cl.
*A61B 17/10* (2006.01)

(52) U.S. Cl.
USPC .......................................................... 606/139

(58) Field of Classification Search
USPC .......................................................... 606/139
See application file for complete search history.

(56) References Cited

U.S. PATENT DOCUMENTS

| | | | |
|---|---|---|---|
| 5,843,099 A | 12/1998 | Nichols et al. | |
| 7,083,636 B2 * | 8/2006 | Kortenbach | 606/220 |
| 2003/0083695 A1 | 5/2003 | Morris et al. | |
| 2005/0177176 A1 * | 8/2005 | Gerbi et al. | 606/139 |

FOREIGN PATENT DOCUMENTS

EP   1498075 A1   1/2005

OTHER PUBLICATIONS

European Search Report dated Feb. 22, 2011 from corresponding European Application No. EP 10251777.8.

* cited by examiner

*Primary Examiner* — Melanie Tyson

(57) ABSTRACT

A tissue anchor applicator includes an end effector assembly having first and second jaw members. The first jaw member includes a pair of spaced-apart arms configured to releasably retain a fastening member thereon. The second jaw member is configured for releasably retaining an anchor member thereon. One (or both) of the first and second jaw members is moveable with respect to the other from a spaced-apart position to an approximated position for securing tissue between the fastening member and the anchor member.

7 Claims, 10 Drawing Sheets

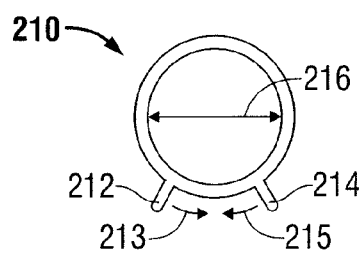
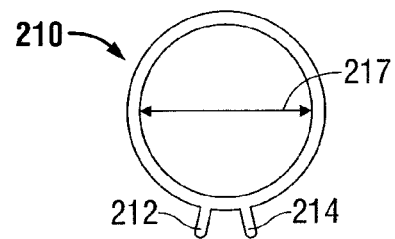
FIG. 11A  FIG. 11B
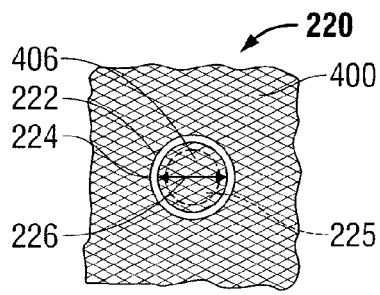
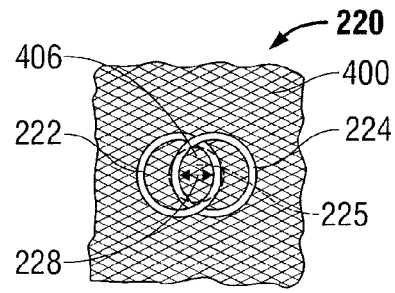
FIG. 12A  FIG. 12B
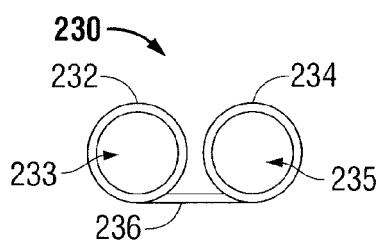
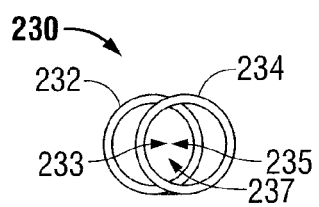
FIG. 13A  FIG. 13B
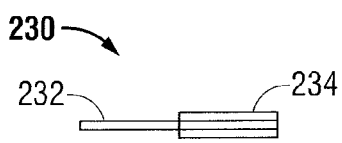
FIG. 13C

TISSUE ANCHOR APPLICATOR

CROSS-REFERENCE TO RELATED APPLICATION

The present application claims the benefit of and priority to U.S. Provisional Application Ser. No. 61/250,070 filed on Oct. 9, 2009, the entire contents of which are incorporated by reference herein.

BACKGROUND

1. Technical Field

The present disclosure relates to a tissue anchor applicator and, more specifically, to a tissue anchor applicator and tissue anchor assemblies for atraumatic attachment of a tissue anchor to tissue.

2. Description of Related Art

As a result of recent technological improvements in surgical instruments, surgical procedures that were previously performed in a conventional or open fashion are now routinely performed using minimally-invasive surgical techniques (e.g., endoscopic, laparoscopic, etc.). Minimally-invasive surgical procedures are less invasive as compared to conventional surgical procedures and, thus, minimize trauma to the patient and reduce patient recovery time.

In endoscopic and laparoscopic surgical procedures, it is often necessary to provide instrumentation to move or manipulate tissue and organs located in or near the area of operation. Generally, laparoscopic surgical procedures involve the introduction of a gas, e.g., carbon dioxide, to insufflate a body cavity, e.g., the abdomen, to provide a working area for the surgeon. More particularly, a trocar device is utilized to puncture the peritoneum to provide an access port by way of a cannula through the abdominal wall. A tube supplying an insufflation gas may then be inserted through the cannula to insufflate the abdomen. The cannula typically includes a fluid-tight seal for maintaining the body cavity in the insufflated condition. Generally, a trocar/cannula is placed through the abdominal wall for introduction of each piece of surgical instrumentation which is necessary to carry out the surgical procedure. In this manner, the surgeon may view the surgical site through an endoscope provided through a first trocar/cannula, and may utilize a second trocar/cannula to introduce a surgical instrument such as a grasper, scissor, clip applier, stapler or any other surgical instrument which may be necessary during the particular surgical procedure.

Although the insufflation gas expands the abdomen to permit the surgeon to view the surgical site, it is often necessary to manipulate internal organs or tissues within the surgical site to provide a clear path to the surgical objective. In the past, surgeons have fastened anchors internally to soft tissue, or viscera, during surgical procedures using hooks or other sharp objects. As can be appreciated, the use of such hooks and other sharp objects may cause great trauma to a patient during the insertion, relocation and/or removal of these anchors.

SUMMARY

In accordance with the present disclosure, a tissue anchor applicator is provided. The tissue anchor applicator includes an end effector assembly having first and second jaw members. The first jaw member includes a pair of spaced-apart arms configured for releasably retaining a fastening member thereon. The second jaw member is configured for releasably retaining an anchor member thereon. One (or both) of the first and second jaw members is moveable with respect to the other from a spaced-apart position to an approximated position for securing tissue between the fastening member and the anchor member.

In one embodiment, the second jaw member is configured to fixedly retain the tissue anchor thereon when the jaw members are disposed in the spaced-apart position. As such, a locking mechanism may be provided for retaining the tissue anchor on the second jaw member when the jaw members are disposed in the spaced-apart position. The second jaw member may further be configured to release the tissue anchor therefrom when the jaw members are moved to the approximated position.

In another embodiment, the spaced-apart arms of the first jaw member are configured to retain a portion of a suture thereon. The suture is configured for securing tissue about the anchor member when the first and second jaw members are moved to the approximated position.

In yet another embodiment, one (or both) of the spaced-apart arms defines a pinch point between the arm and a distal end of the arm. The pinch point releasably retains the portion of the suture on the arm. The pinch point is configured such that, when a pre-determined pulling force is applied to the suture, the portion of suture releasably retained by the pinch point is released from the arm, i.e., the suture is pulled through the pinch point, releasing the suture from the arm.

In still another embodiment, the end effector assembly is disposed at a distal end of a shafted instrument. The shafted instrument may include an actuator for moving the jaw members from the spaced-apart position to the approximated position.

In still yet another embodiment, the securing member includes a ring structure having a suture coupled thereto for securing tissue between the ring structure and the anchor member.

A tissue anchor assembly in accordance with another embodiment of the present disclosure includes an anchor member and a fastening member. The anchor member includes a ball portion, a base, and a shaft interconnecting the ball portion and the base. The anchor member is positionable adjacent a face of tissue. The fastening member is positionable adjacent an opposite face of tissue and includes a pair of spaced-apart arcuate arms connected to each other at first ends thereof and having free second ends. One (or both) of the arms is moveable with respect to the other between an at-rest position and an expanded position. In the expanded position, the arms define a first gap distance therebetween, while, in the expanded position, the arms define a second gap distance therebetween that is greater than the first gap distance. Accordingly, when in the expanded position, the fastening member is positionable about the shaft of the anchor member. Once positioned about the shaft of the anchor member, the fastening member may be returned to the at-rest position for fixedly securing tissue between the anchor member and the fastening member.

In accordance with another embodiment of the present disclosure, a tissue anchor assembly including an anchor member and a fastening member is provided. The anchor member is positionable adjacent a face of tissue and may be configured according to any of the embodiments described above. The fastening member defines an opening extending therethrough and is positionable adjacent an opposite face of tissue. The fastening member is transitionable from an at-rest position to an expanded position. When in the expanded position, the ball portion of the anchor member may be passed through the opening of the fastening member. Once the ball portion has passed through the opening of the fastening member, the fastening member may be transitioned back to the at-rest position for retaining the fastening member about the shaft between the ball portion and the base, thereby fixedly securing tissue between the anchor member and the fastening member.

In one embodiment, the fastening member includes a deformable ring. The ring is resiliently deformable from the at-rest position, wherein the ring defines a generally elliptical configuration, to the expanded position, wherein the ring defines a generally circular configuration. To deform the ring from the at-rest position to the expanded position, the ring is squeezed, or pinched at diametric positions along a circumference thereof.

In another embodiment, the fastening member includes pinching ring having first and second tabs. One (or both) of the tabs is moveable with respect to the other between the at-rest position and the expanded position. In the at-rest position, the pinching ring defines a first diameter. In the expanded position, the pinching ring defines a second diameter that is greater than the first diameter.

In yet another embodiment, the fastening member includes two (or more) rings. The rings are transitionable between the at-rest position, wherein the rings are at least partially spaced-apart with respect to one another, and the expanded position, wherein the rings are further overlapping with respect to one another.

In accordance with still another embodiment of the present disclosure, a tissue anchor assembly including an anchor member and a fastening member is provided. The anchor member may be configured according to any of the embodiments discussed above. The fastening member is positionable adjacent an opposite face of tissue as the anchor member and includes a ring structure defining an opening extending therethrough and a suture. The suture is coupled to the ring structure and is moveable between a first position and a second position. In the first position, the ball portion of the anchor member is passable through the opening of the ring structure. In the second position, once the anchor member has passed through the opening of the ring structure, the fastening member is fixedly retained about the shaft between the ball portion and the base to fixedly secure tissue between the anchor member and the fastening member.

In one embodiment, the ring structure includes a plurality of expandable members coupling the suture to the ring structure. The plurality of expandable members is transitionable between an at-rest position corresponding to the first position of the suture and an expanded position corresponding to the second position of the suture.

In another embodiment, the ring structure includes a slot defined therethrough. The slot extends at least partially around a circumference of the ring structure. The suture is disposed through the slot defined within the ring structure and is moveable through the slot between the first position, wherein the suture is disposed at a first end of the slot, and the second position, wherein the suture is disposed at a second end of the slot.

In yet another embodiment, the ring structure includes first and second rings rotatably coupled to one another. One (or both) of the rings is rotated with respect to the other for transitioning the suture between the first position and the second position.

In still another embodiment, a middle portion of the suture is fixedly secured to the ring structure, while first and second ends of the suture extend through an aperture defined at an opposite end of the ring structure. The first and second ends of the suture are selectively tensionable for transitioning the suture from the first position to the second position.

In still yet another embodiment, the ring structure includes a tube having a lumen extending therethrough and the suture defines a loop that is tightenable from an open position to a cinched position upon movement of the suture from the first position to the second position. The tube is disposed about a first portion of the loop when the suture is disposed in the first position (when the loop is in the open position), and is disposed about a second, larger portion of the loop when the suture is disposed in the second position (when the loop is in the cinched position). Further, the tube may define a circular, ovular, triangular, rectangular, pentagonal, hexagonal, octagonal, or dodecagonal cross-sectional shape, although other cross-sectional shapes are also contemplated.

BRIEF DESCRIPTION OF THE DRAWINGS

Various embodiments of the subject tissue anchor assemblies and tissue anchor applicators are described herein with reference to the drawings wherein:

FIG. 11A is a top view of another embodiment of a fastening member for use with the anchor member of FIG. 7, wherein the fastening member is disposed in a first position;

FIG. 11B is a top view of the fastening member of FIG. 11A shown in a second position;

FIG. 12A is a top view of yet another embodiment of a fastening member for use with the anchor member of FIG. 7, wherein the fastening member is positioned adjacent tissue in a first position;

FIG. 12B is a top view of the fastening member of FIG. 12B shown in a second position for fixing the anchor member to tissue;

FIG. 13A is a top view of still another embodiment of a fastening member for use with the anchor member of FIG. 7, wherein the fastening member is disposed in a first position;

FIG. 13B is a top view of the fastening member of FIG. 12A shown in a second position;

FIG. 13C is a side view of the fastening member of FIG. 12A shown in the first position;

DETAILED DESCRIPTION

Figure 1:
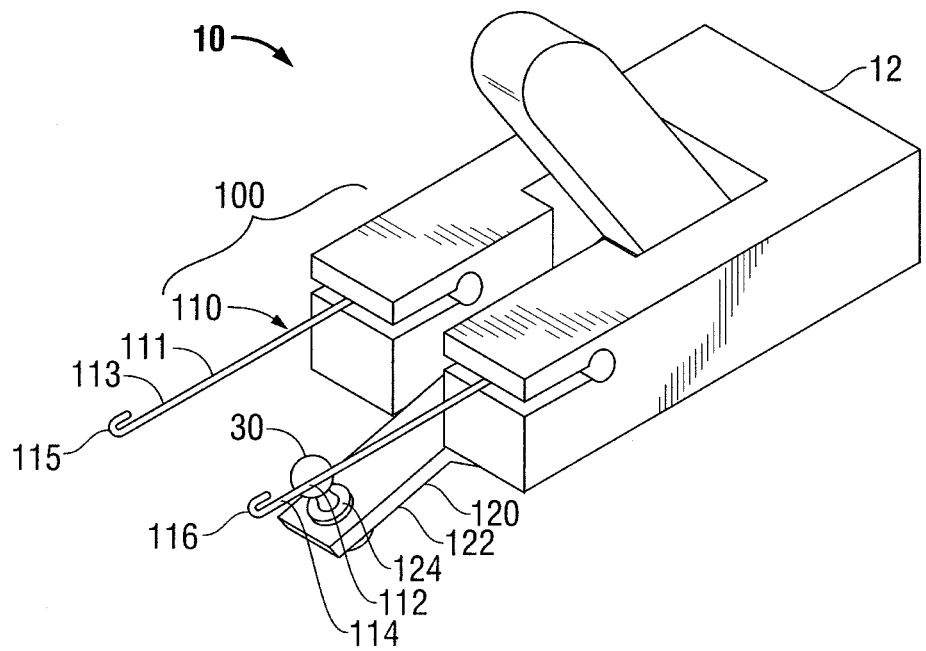
FIG. 1 is a perspective view of a tissue anchor applicator in accordance with one embodiment of the present disclosure shown including a pair of jaw members disposed in a spaced-apart position.

Turning now to FIG. 1, a tissue anchor applicator 10 is shown generally including a housing 12 having an end effector assembly 100 disposed at a distal end thereof. However, end effector assembly 100 need not be engaged to housing 12, but may be disposed at a distal end of a shafted instrument 300 (see FIG. 22) or may be disposed in any other suitable configuration. End effector assembly 100 includes first and second jaw members 110, 120, respectively. First jaw member 110 includes a pair of spaced apart arms 111, 112 extending from a distal end of housing 12. Arms 111, 112 each define a suture retaining portion 115, 116, respectively, at respective distal ends 113, 114 thereof. Suture retaining portions 115, 116 will be discussed in more detail below. Second jaw member 120 includes an anchor retaining portion 124 disposed at a distal end 122 thereof for retaining an anchor member 30 thereon.

Figure 4:
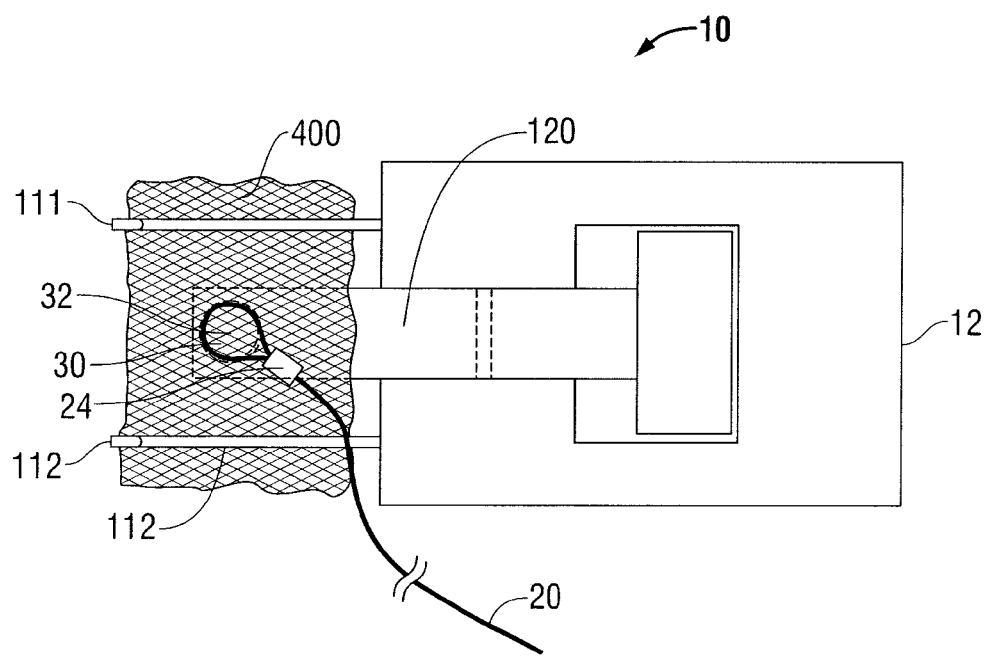
FIG. 4 is a top view of the tissue anchor applicator of FIG. 1 wherein the jaw members are disposed in an approximated position.
Figure 5:
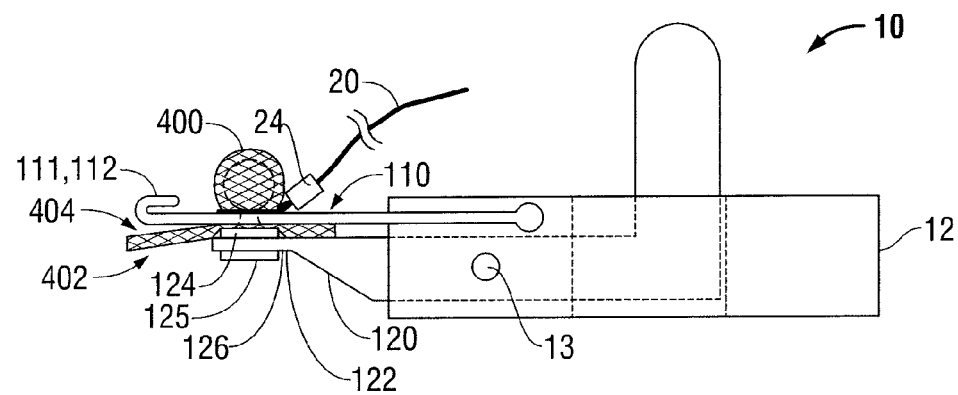
FIG. 5 is a side view of the tissue anchor applicator of FIG. 1, wherein the jaw members are disposed in the approximated position.

As shown in FIG. 1, jaw members 110 and 120 of end effector assembly 100 are disposed in a spaced-apart position. Jaw member 120 is moveable relative to jaw member 110 from the spaced-apart position shown in FIG. 1 to an approximated position, as shown in FIGS. 4 and 5, although it is envisioned that jaw member 110 be moveable relative to jaw member 120, or that both jaw members 110, 120 be moveable with respect to one another between the spaced-apart position and the approximated position. Further, it is envisioned that the orientation of jaw members 110, 120 be reversed, e.g., jaw member 120 may be disposed above jaw member 110 when in the spaced-apart position.

Figure 2:
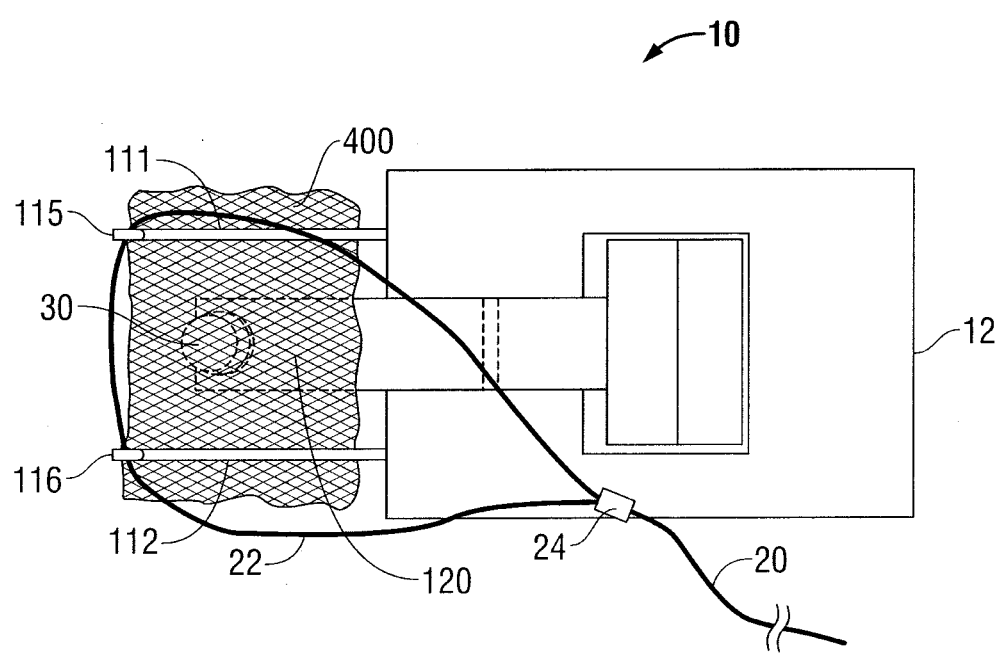
FIG. 2 is a top view of the tissue anchor applicator of FIG. 1 wherein the jaw members are disposed in the spaced-apart position.
Figure 3:
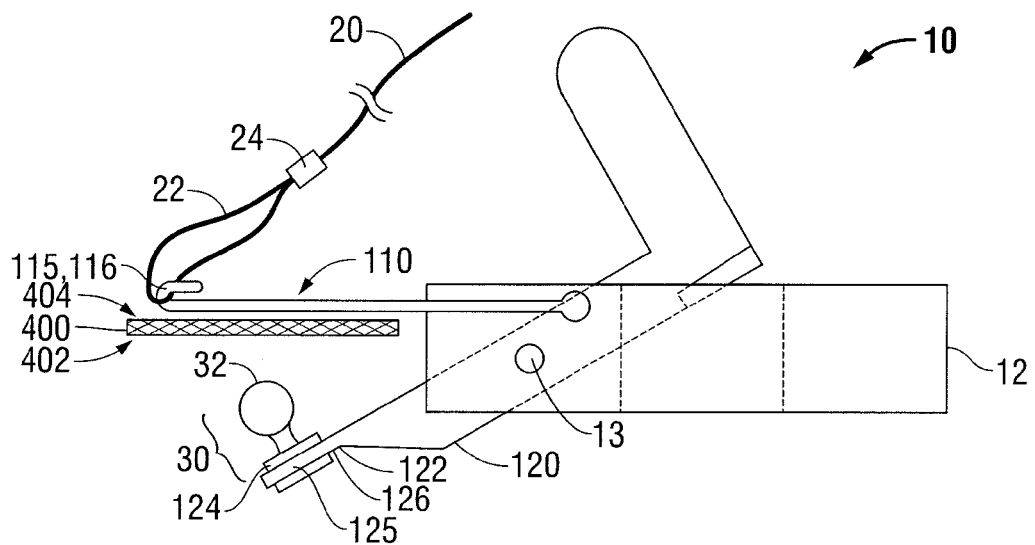
FIG. 3 is a side view of the tissue anchor applicator of FIG. 1 wherein the jaw members are disposed in the spaced-apart position.

Referring now to FIGS. 2-3, jaw members 110, 120 of tissue anchor applicator 10 are shown disposed in the spaced-apart position with tissue 400 disposed therebetween. Each arm 111, 112 of jaw member 110 retains a portion of suture loop 22 of suture 20 thereon. More specifically, suture loop 22 is disposed through suture retaining portions 115, 116 of arms 111, 112, respectively. Cinch knot 24, which is formed along suture 20, is configured for bi-directional movement along suture 20 for loosening and tightening suture loop 22, i.e. for increasing or decreasing the diameter of suture loop 22.

As shown in FIGS. 2-3, anchor member 30 is retained on anchor retaining portion 124 of second jaw member 120 at distal end 122 thereof. Anchor member 30 includes a ball portion 32, a base 34 and a shaft 33 (FIG. 7) interconnecting ball portion 32 and base portion 34. Base 34 of anchor member 30 is engaged to anchor retaining portion 124 of second jaw member 120, while shaft 33 (FIG. 7) and ball portion 32 extend therefrom toward jaw member 110 such that ball portion 32 is positioned adjacent tissue 400.

Anchor member 30 may be releasably retained on jaw member 120 by any suitable mechanism, e.g., a releasable clamp 125. Anchor retaining portion 124 of jaw member 120 may be configured to fixedly retain anchor member 30 thereon when jaw members 110 and 120 are disposed in the spaced-apart position. This may be accomplished, for example, by a locking mechanism 126 that prevents the release of anchor member 30 until jaw members 110, 120 are disposed in the approximated position. Alternatively, anchor retaining portion 124 may be configured to fixedly retain anchor member 30 thereon until a user-activated release mechanism (not shown) is engaged. Further, a second locking mechanism (not shown) may be provided for maintaining jaw members 110 and 120 in the spaced-apart position (and/or the approximated position). For example, a locking pin (not shown) may be inserted into aperture 13 of housing 12 to inhibit movement of jaw member 120, thereby fixing the relative position of jaw members 110, 120. Upon removal of the locking pin (not shown) jaw member 120 would once again be permitted to move between the spaced-apart and approximated positions. Such a feature helps ensure that jaw member 120 is not moved to the approximated position accidentally.

With reference now to FIGS. 3-5, the operation of tissue anchor applicator 10 will be described in detail. Initially, in order to load tissue anchor applicator 10 for use, jaw members 110, 120 are moved to the spaced-apart position, anchor member 30 is secured to anchor retaining member 124 of jaw member 120, and suture loop 22 is disposed through arms 111, 112 of jaw member 110. With tissue anchor applicator 10 loaded for use, end effector assembly 100 of anchor applicator 10 is positioned as described above and as shown in FIG. 3, such that tissue 400 is disposed between jaw members 110 and 120 with ball portion 32 of anchor member 30 disposed adjacent a first face, or surface 402 of tissue 400 and with suture loop 22 disposed adjacent second face, or surface 404 of tissue 400.

With end effector assembly 100 positioned as described above, jaw member 120 may be moved from the spaced-apart position to move to the approximated position, such that anchor member 30 is advanced toward tissue 400 and jaw member 110. As jaw member 120 is moved further toward the approximated position, ball portion 32 of anchor member 30 eventually contacts first surface 402 of tissue 400. Further movement of jaw member 120 toward the approximated position urges ball portion 32 of anchor member 30 into tissue 400 such that tissue 400 is similarly urged toward jaw member 110. As anchor member 30 urges tissue 400 toward first jaw member 110, arms 111, 112 of first jaw member 110 inhibit the movement of tissue 400, allowing ball portion 32 of anchor member 30 to engage face 402 of tissue 400, creating a bulge in tissue 400 protruding from face 404 of tissue 400 toward jaw member 110 in the vicinity of where ball portion 32 of anchor member 30 is urged into tissue 400. Eventually, as jaw member 120 approaches the approximated position, anchor member 30 is urged further toward jaw member 110 such that the bulge of tissue protruding from tissue 400 and ball portion 32 of anchor member 30 extend between arms 111 and 112 of jaw member 110. When jaw member 120 reaches the approximated position with respect to jaw member 110, anchor member 30 and, thus, the bulge of tissue 400 surrounding anchor member 30 is disposed between arms 111 and 112 of jaw member 110 and through suture loop 22 retained on arms 111, 112.

Once jaw members 110 and 120 have reached the approximated position such that anchor member 30 and tissue 400 surrounding anchor member 30 are disposed between arms 111, 112 of jaw member 110 and through suture loop 22, suture 20 may be pulled proximally, thereby dislodging, or disengaging suture loop 22 from suture retaining portions 115, 116 of arms 111, 112, respectively. As suture 20 is released from suture retaining portions 115, 116 of arms 111, 112, respectively, suture loop 22 beings to cinch about shaft 33 of anchor member 30 between ball portion 32 and base 34 thereof due to the relative positioning of anchor member 30 and suture loop 22 when jaw members 110, 120 are disposed in the approximated position.

As suture 20 is pulled further proximally, suture loop 22 is cinched about shaft 33 of anchor member 30, fixedly securing tissue therebetween. More particularly, as suture 20 is pulled proximally, cinch knot 24 is translated along suture 20 reducing the diameter of suture loop 22 such that suture loop 22 is cinched, or tightened snugly about shaft 33 of anchor member 30 with bulge in tissue 400 disposed therebetween. As such, tissue 400 is fixedly disposed between anchor member 30 and suture loop 22. Further, due to the configuration of anchor member 30, suture loop 22 is inhibited from sliding off, or disengaging anchor member 30 when suture loop 22 is cinched about shaft 33 due to the configuration of anchor member 30, i.e., since shaft 33 extends between and defines a smaller diameter than ball portion 32 and base 34 of anchor member 30.

Once suture loop 22 is cinched around shaft 33 and the bulge in tissue 400, anchor member 30 may be released from the tissue anchor retaining portion 124 of jaw member 120, e.g., by releasing clamp 125. As mentioned above, anchor member 30 may be released from tissue anchor retaining portion 124 of jaw member 120 automatically upon approximation of jaw members 110, 120, or may be released manually. Finally, with suture 20 fixedly securing tissue 400 about tissue anchor 30, and with tissue anchor 30 disengaged from jaw member 120, tissue anchor applicator 10 may be removed from the surgical site.

With tissue 400 fixedly retained between suture loop 22 and anchor member 30, suture 20 may be manipulated in order to retract tissue 400, thereby providing access to tissue and/or organs in and around tissue 400. As can be appreciated, due to the positioning of ball portion 32 on face 402 of tissue 400 and suture loop 22 cinched about shaft 33 between ball portion 32 and base 34 on an opposite face 404 of tissue 400, there is a reduced risk of slippage or disengagement of suture loop 22 from anchor member 30 upon manipulation of suture 20.

Referring now to FIGS. 6A-6D, several embodiments of suture retaining portions 115, 116 configured for retaining suture 20 at distal ends 113, 114 of arms 111, 112, respectively, are shown. Although only one arm 111 is shown, the configurations of FIGS. 6A-6D are similarly applicable to both arms 111 and 112 of jaw member 110. For ease of reference, and to avoid repetition, the configurations of FIGS. 6A-6D will be discussed in relation to arm 111, keeping in mind that similar configurations are contemplated for arm 112.

Figure 6A:
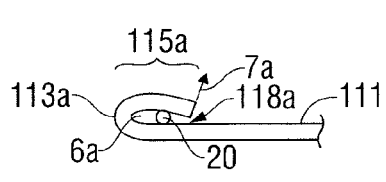
FIG. 6A is a side view of one embodiment of a suture retaining member for use with the tissue anchor applicator of FIG. 1.

A first configuration is shown in FIG. 6A in which suture retaining portion 115a is defined by a distal portion 113a of arm 111, which is curved, or bent back onto arm 111 to define an aperture 6a therebetween. A pinch point 118a is created between distal end 113a of arm 111 and the remaining body portion of arm 111 when suture retaining member 115a is disposed in an at-rest position. Suture 20 is disposed through aperture 6a defined by distal portion 113a and arm 111 and is retained therein by the pinched-closed suture retaining member 115a. When suture 20 is pulled proximally, e.g., to fixedly engaging anchor member 30 to tissue 400 (see FIG. 5), suture 20 initially contacts pinch point 118a. When a sufficient proximal pulling force is applied to suture 20, suture 20 is urged between distal end 113a of arm 111 and arm 111, deflecting distal end 113a of arm 111 in the direction of arrow 7a, i.e., away from arm 111, creating an opening at pinch point 118a. When distal end 113a is urged a sufficient distance in the direction of arrow 7a, suture 20 is able to slide through pinch point 118a, releasing suture 20 from suture retaining member 115a. Once suture 20 is released from suture retaining portion 115a, distal end 113a returns to the at-rest position shown in FIG. 6A.

Figure 6B:
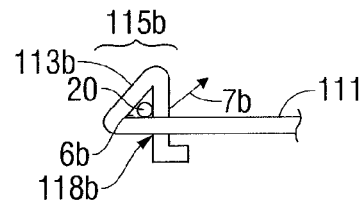
FIG. 6B is a side view of another embodiment of a suture retaining member for use with the tissue anchor applicator of FIG. 1.

A second configuration is shown in FIG. 6B, wherein distal end 113b of arm 111 is curved, or bent to define suture retaining portion 115b having a generally triangular-shaped aperture 6a. More particularly, distal end 113b of arm 111 contacts arm 111 at pinch point 118b to retain suture within aperture 6b while in an at-rest position. As in the previous embodiment, proximal pulling of suture 20 causes suture 20 to contact distal end 113b of arm 111 at pinch point 118b, deflecting distal end 113b of arm 111 in the direction of arrow 7b. Upon application of a sufficient pulling force, suture 20 deflects distal end 113b away from contact point 118b a sufficient distance to create an opening for passage of suture 20 therethrough, releasing suture 20 from suture retaining portion 115b. Once suture 20 is released from suture retaining portion 115*b*, suture 20 may be further translated along arm 111 to cinch around tissue 400, as described above (see FIG. 5). Arm 111 provides a smooth camming surface for suture 20 to slide along and acts as a guide for suture 20 to help ensure proper placement of suture 20 about tissue 400 and anchor member 30 (see FIG. 5). At the same time, once suture 20 passes through pinch point 118*b*, distal end 113*b* of arm 111 is returned to the at-rest position, once again contacting arm 111 to create pinch point 118*b*, as shown in FIG. 6B.

Figure 6C:
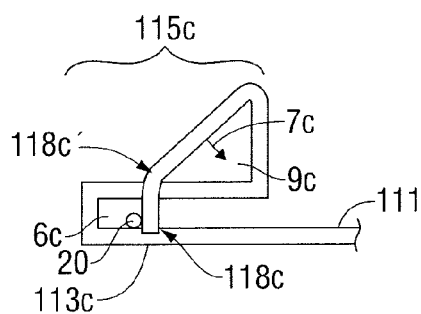
FIG. 6C is a side view of yet another embodiment of a suture retaining member for use with the tissue anchor applicator of FIG. 1.

A third configuration of a suture retaining portion 115*c* is shown in FIG. 6C wherein distal end 113*c* of arm 111 is bent with respect to arm 111 to define a generally rectangular aperture 6*c* and a generally triangular aperture 9*c* therebetween. More particularly, distal end 113*c* of arm 111 is configured such that two pinch, or contact points are formed: a first contact point 118*c* between distal end 113*c* and arm 111 and a second contact point 118*c*' between rectangular aperture 6*c* and triangular aperture 9*c*. As shown in FIG. 6C, suture 20 is disposed through rectangular aperture 6*c*. Thus, as in the previous embodiments, when suture 20 is pulled proximally, distal end 113*c* of arm 111 is deflected in the direction of arrow 7*c*, moving distal end 113*c* away from contact point 118*c*, eventually permitting suture 20 to pass therebetween, releasing suture 20 from suture retaining portion 115*c*. Upon release of suture 20, distal end 115*c* returns to its initial position as described above. As with the previous embodiments, arm 111 provides a smooth guide, or cam surface for suture 20 to help ensure proper placement of suture 20 as suture 20 is cinched about tissue 400 (see FIG. 5).

Figure 6D:
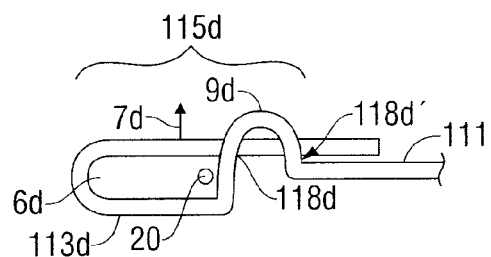
FIG. 6D is a side view of still another embodiment of suture retaining member in accordance with one embodiment of the present disclosure.

A fourth configuration of a suture retaining portion 115*d* is shown in FIG. 6D wherein distal end 113*d* of arm 111 is bent back onto arm 111 to define an aperture 6*c* therebetween for retaining suture 20 therein. Suture retaining portion 115*d* further includes a hump 9*d* contacting distal end 113*d* of arm 111 to define first and second pinch points 118*d*, 118*d*', respectively, when in an at-rest position. As suture 20 is pulled proximally, suture 20 contacts hump 9*d* and distal end 113*d*, deflecting distal end 113*d* in the direction of arrow 7*d*. When a sufficient pulling force is exerted on suture 20, distal end 113*d* is deflected away from hump 9*d*, thereby creating an opening between first and second pinch points 118*d* and 118*d*' for passage of suture 20 therethrough, releasing suture 20 from suture retaining portion 115*d*. Once released, suture retaining portion 115*d* returns to its at-rest position, while suture 20 is slid over hump 9*d* and along arm 111 to cinch about tissue 400 (FIG. 5). Suture 20 may also be releasably engaged with suture retaining portion 115 by other obstructive or mechanical means known to those of skill in the art.

Embodiments of the tissue anchor assembly of the present disclosure will now be discussed with reference to FIGS. 7-21. Generally, the tissue anchor assembly includes an anchor member 30 and a fastening member, e.g., fastening member 40. Anchor member 30, shown in FIG. 7, includes ball portion 32, shaft 33 extending therefrom and base portion 34 disposed on shaft 33. Alternatively, the anchor member may simply be a ball anchor 32 wherein shaft 33 and base portion 34 have been eliminated. Anchor member 30 is positionable about a face of tissue oriented such that ball portion 30 is closest to a face of tissue. Continual reference to anchor member 30 and FIG. 7 will be made during discussion of the specific embodiments of the fastening member hereinbelow. It is envisioned that tissue may be secured to anchor member 30 and/or ball anchor 32 by any of the fastening members discussed below and shown in FIGS. 8-21.

The fastening member, different embodiments of which will be described in detail below, is positionable about an opposing face of tissue and is disposable around the shaft 33 between the ball portion 32 and the base 34. The fastening member is fastened around shaft 33, with tissue 400 disposed therebetween, securing tissue 400 around anchor member 30, to create an atraumatic, retractable tissue anchor. In embodiments where ball anchor 32 is used, the fastening member is positioned about an opposing face of tissue and cinched around tissue 400 such that a portion of tissue 400 is secured around the ball anchor 32. A suture connected to the fastening member may then be used to retract tissue.

Figure 8:
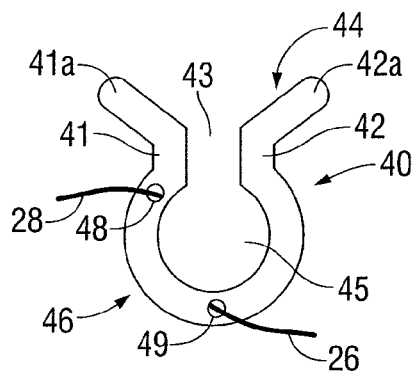
FIG. 8 is a top view of a clip member for use with the anchor member of FIG. 7.
Figure 9:
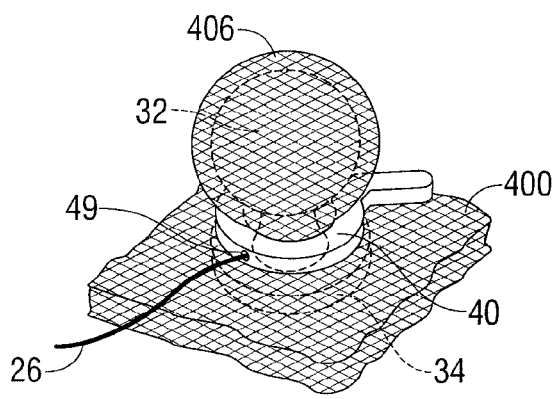
FIG. 9 is perspective view of the clip member of FIG. 8 shown fixing tissue about the anchor member of FIG. 7.

One embodiment of the fastening member is shown in FIGS. 8-9, wherein the fastening member includes a "C"-shaped clip 40. Clip 40 includes a pair of arcuate arms 41 and 42 including diverging fingers 41*a* and 42*a*, respectively, defining a gap 43 therebetween at distal end 44 of clip 40. Fingers 41*a* and 42*a* of arcuate arms 41 and 42, respectively, are biased towards each other. Gap 43 of clip 40 is expandable from a first, at-rest state, to a second, expanded state, for acceptance of shaft 33 of anchor member 40 therethrough. Central bore 45 is located though a center of clip 40 and is dimensioned to allow shaft 33 of anchor member 30 to be disposed therethrough. A first aperture 48 is defined in clip 40 adjacent distal end 44 of clip 40 and a second aperture 49 is defined in clip 40 adjacent proximal end 46 of clip 40. First aperture 48 is configured for acceptance of a removal suture 26 therethrough and second aperture 49 is configured for acceptance of a retraction suture 28 therethrough, the operation of both of which will become more apparent below.

Figure 7:
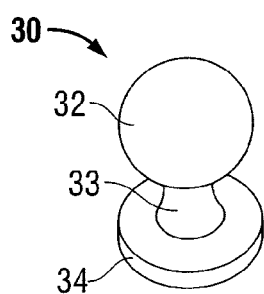
FIG. 7 is perspective view of an anchor member in accordance with one embodiment of the present disclosure.

Referring now to FIG. 9 in conjunction with FIGS. 7-8, when anchor member 30 is positioned adjacent a face of tissue 400, clip 40 may be disposed about shaft 33 of anchor member 30 from an opposing face of tissue 400, thereby fixing a portion 406 of tissue 400 about anchor member 30.

In operation, gap 43 formed between fingers 41*a* and 42*a* of clip 40 is expanded as distal end 44 of clip 40 is urged into contact with tissue 400 (with shaft 33 disposed on an opposing face of tissue 400). Gap 43 is expandable a sufficient distance such that portion 406 of tissue 400 and shaft 33 may slide through gap 43 and into central bore 45 of clip 40. Once shaft 33, with portion 406 of tissue disposed therearound, is positioned within bore 45, fingers 41*a*, 42*s* are not longer being urged apart, allowing clip 40 to return to the at-rest state, e.g., wherein gap 43 returns from the expanded state back to the initial state. As can be appreciated, a diameter of gap 43 in this first state is sufficiently small to prevent shaft 33 and portion 406 of tissue 400 from sliding out of central bore 45. Similarly, clip 40 is prevented from sliding axially along shaft 33 because a diameter of central bore 45, when clip 40 is in the first-state, is less than a diameter of both ball portion 32 and base portion 34, i.e., clip 40 is retained on shaft 33 between ball portion 32 and base portion 34. Thus, clip 40, anchor member 30 and portion 406 of tissue 400 are all held in place relative to one another, thereby creating a tissue anchor. Suture 28 may then be manipulated to retract tissue 400, providing greater access to nearby and underlying tissue and organs. When it is desired to remove the tissue anchor, removal suture 26 may be pulled such that tissue portion 406 and shaft 33 urge the expansion of gap 43 of clip 40, to permit passage therethrough. More particularly, removal suture 26 is attached to clip 40 directly opposite gap 43 such that when removal suture 26 is pulled proximally, clip 40 is pulled proximally with respect to shaft 33 such that shaft 33 contacts arcuate arms 41 and 42 and urges arms 41 and 42 apart from one another, widening gap 43. Eventually, as mentioned above, gap 43 is widened a sufficient amount such that shaft 33 and tissue portion 406 can pass therebetween, releasing clip 40 from shaft 33.

Figure 10A:
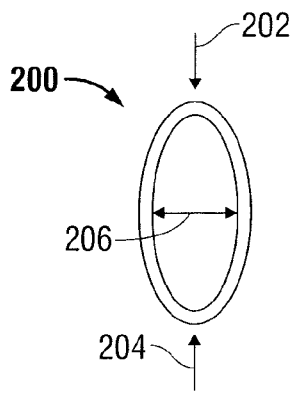
FIG. 10A is a top view of one embodiment of a fastening member for use with the anchor member of FIG. 7, wherein the fastening member is disposed in a first position.
Figure 10B:
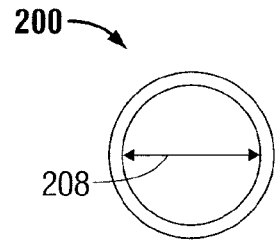
FIG. 10B is a top view of the fastening member of FIG. 10A shown in a second position.

FIGS. 10A-10B show another embodiment of a fastening member including a partially deformable elliptical ring 200. Ring 200 is biased to form an elliptical shape (FIG. 10A) having a short diameter 206 in an at-rest position. Short diameter 206 is smaller than a diameter of ball portion 32 and is also smaller than a diameter of base portion 34 of anchor member 30. Thus, once ring 200 is positioned about shaft 33 and allowed to return to its at-rest position, as will be discussed below, ring 200 is inhibited from sliding along shaft 33 due to its positioning between ball portion 32 and base portion 34. Accordingly, ring 200 is fixedly securable about tissue 400 disposed around anchor member 30 for forming a tissue anchor.

In order to move ring 200 into position about shaft 33 of anchor member 30, ring 200 is deformed by pinching at diametric positions 202 and 204 thereof to deform ring 200 to a generally circular shape (FIG. 10B). When pinched into this circular shape, ring 200 defines a diameter 208 which is sufficiently large to allow ring 200 to pass over ball portion 32 of anchor member 30. Thus, once anchor member 30 is positioned adjacent a face of tissue, ring 200 may be deformed as described above such that ring 200 may pass over ball portion 32 from an opposing face of tissue 400 to secure a portion 406 of tissue 400 on anchor member 30. More specifically, once ring 200 has passed over ball portion 32, the pinch may be released, allowing ring 200 to return back to its at-rest, elliptical configuration to fasten ring 200 about shaft 33 between ball portion 32 and base portion 34, securing tissue around anchor member 30. To remove the tissue anchor, ring 200 is once again pinched at positions 202 and 204 to deform ring 200 to the circular shape (see FIG. 10B) such that ring 200 may then be slid over ball portion 32, disengaging the tissue anchor. Suture material (not shown) may be coupled to ring 200 to permit retraction of tissue 400 once the anchor member 30 and ring 200 are fixedly secured about tissue 400.

Referring now to FIGS. 11A-11B, another embodiment of a fastening member is shown including a ring 210 having first and second tabs 212 and 214 extending therefrom. More specifically, ring 210 is formed of one or more revolutions of wire having tab 212 extending from a first end thereof and having tab 214 extending from a second end thereof. Ring 210 is biased toward a first position wherein tabs 212 and 214 are spaced-apart relative to one another and wherein ring 210 defines a first diameter 216. Tabs 212 and 214 are moveable in the direction of arrows 213 and 215, respectively, e.g., toward one another, to a second, or closer-together position wherein ring 210 defines a second diameter 217. Second diameter 217 is larger than first diameter 216. As such, ring 210 is configured such that first diameter 216, e.g., when tabs 212 and 214 are disposed in the spaced-apart position, is sufficiently small to inhibit ring 210 from passing over ball portion 32 or base portion 34 of anchor member 30. On the other hand, when tabs 212 and 214 are moved toward each other, e.g., to the second position, to define second diameter 217, the diameter 217 of ring 210 is sufficiently large to permit ring 210 to pass over ball portion 32 of anchor member 30.

Thus, in operation, tabs 212 and 214 are squeezed in the direction of arrows 213 and 215, respectively, and ring 210 is passed over ball portion 32 of anchor member 30 such that ring 210 is positioned adjacent shaft 33 between ball portion 32 and base portion 34, with portion 406 of tissue 400 disposed therebetween. Then, tabs 212 and 214 are released, allowing ring 210 to return to the first, or at-rest position wherein tabs 212, 214 are disposed in the spaced-apart position, such that ring 210 fixedly secures portion 406 of tissue 400 around anchor member 30. Due to the smaller diameter 216 when tabs 212 and 214 of ring 210 are disposed in the spaced-apart position, ring 210 is fixed between ball portion 32 and base portion 34. For removal, tabs 212 and 214 are once again squeezed in the direction of arrows 213 and 215, respectively, expanding ring 210 to permit ring 210 to pass back over ball portion 32 of anchor member 30.

FIGS. 12A-12B illustrate another embodiment of a fastening member 220 of the present disclosure, the fastening member 220 including a pair of rings 222 and 224 (collectively rings 220). Rings 222 and 224 are biased toward a generally spaced-apart position, as shown in FIG. 12B, such that the overlapping rings 222 and 224 form an opening 225 therebetween. Rings 222 and 224 are moveable with respect to each other from this first position shown in FIG. 12B to a further overlapping (or substantially overlapping) position, as shown in FIG. 12A. When rings 222 and 224 are moved to this further overlapping position, the opening 225 through the overlapping rings 222 and 224 has a diameter 226 that is greater than the opening 225 when the rings 220 are in the spaced-apart position. When in the further overlapping position, opening 225 is sufficiently large to allow rings 220 to pass over the ball portion 32 of anchor member 30 (see FIG. 7). When released, the biasing of rings 222 and 224 to the spaced-apart state urges rings 220 to move apart from each other, resulting in opening 225 having a diameter 228 being substantially identical to the diameter of shaft 33 when disposed therearound, inhibiting rings 220 from sliding along shaft 33 and from passing over ball portion 32 or base portion 34 of anchor member 30.

To fasten portion 406 of tissue 400 around anchor member 30 using rings 220, the anchor member 30 is positioned adjacent a face of tissue 400 and rings 220 are positioned adjacent an opposing face of tissue 400. As discussed above, rings 220, when at-rest, are disposed the spaced-apart position. In order for rings 220 to pass over ball portion 32, rings 220 are moved into the further overlapping position, as shown in FIG. 12A and as described above. Rings 220 are then passed over ball portion 32 of anchor member 30, with portion 406 of tissue 400 disposed therebetween. Once rings 220 have passed over ball portion 32 and are positioned about the shaft 33, rings 220 can be released, allowing the rings 222 and 224 to return to the biased, spaced-apart position. As rings 222 and 224 move back to this spaced-apart position, opening 225 decreases until the diameter 228 of opening 225 is substantially identical to the diameter of shaft 33 such that portion 406 of tissue is fixedly secured about anchor member 30 between ball portion 32 and base portion 34.

As shown in the embodiment of FIGS. 13A-13C, rings 232 and 234 (collectively rings 230) may be formed from a single wire 230 wherein rings 232 and 234 are connected via straight portion 236. Forming rings 232 and 234 from a single wire 230 allows rings 232 and 234 to be biased toward a spaced-apart state, or position as discussed above in relation to rings 220. FIG. 13A shows rings 230 disposed in the spaced-apart state wherein ring 232 defines central aperture 233 therethrough and ring 234 defines central aperture 235 therethrough. FIG. 13B shows rings 232 and 234 being moved to the further overlapping state, or position in which central apertures 233 and 235 of rings 232 and 234, respectively, are moved into alignment with each other. When central apertures 233 and 235 are aligned, the resulting opening 237 is sufficiently large to allow rings 230 to pass over ball portion 32 of anchor member 30 (See FIG. 7). As discussed above in connection with rings 220, when rings 230 are allowed to move back to the spaced-apart position, opening 237 decreases in diameter as rings 232, 234 are moved apart from one another until opening 237 is substantially identical to the diameter of shaft 33, thereby fixedly securing portion 406 of tissue 400 about anchor member 30. FIG. 13C shows a side view of rings 230 when disposed in the spaced apart position.

Figure 14A:
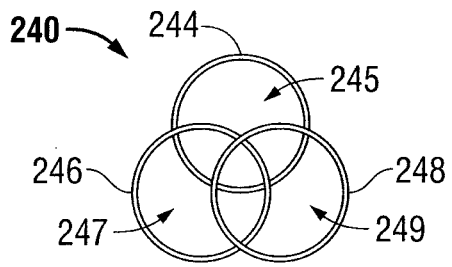
FIG. 14A is a top view of still yet another embodiment of a fastening member for use with the anchor member of FIG. 7, wherein the fastening member is disposed in a first position.
Figure 14B:
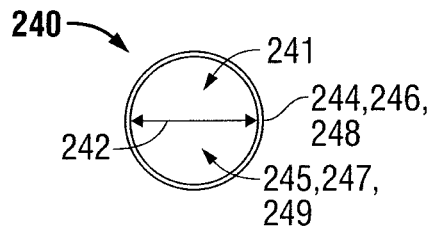
FIG. 14B is a top view of the fastening member of FIG. 14A shown in a second position.

Alternatively, three rings 244, 246 and 248 may be provided, functioning in a substantially similar manner as the two ring configurations 220 and 230. Specifically, rings 240 are biased toward a first, spaced-apart state as shown in FIG. 14A wherein ring 244 defines aperture 245 therethrough, ring 246 defines aperture 247 therethrough and ring 248 defines aperture 249 therethrough. Rings 240 are moveable from this first state to a further overlapping or second state, shown in FIG. 14B wherein apertures 245, 247 and 249 of rings 244, 246 and 248, respectively, are brought into alignment with each other to form opening 241 having a diameter 242. Diameter 242 of opening 241 is large enough to allow rings 240 to pass over ball portion 32 of anchor member 30 when rings 240 are moved into the second state. Once rings 240 have passed over ball portion 32 of anchor member 30 and are positioned about shaft 33, rings 240 may be returned to the spaced-apart state to fixedly secure portion 406 of tissue 400 about anchor member 30.

Figure 15:
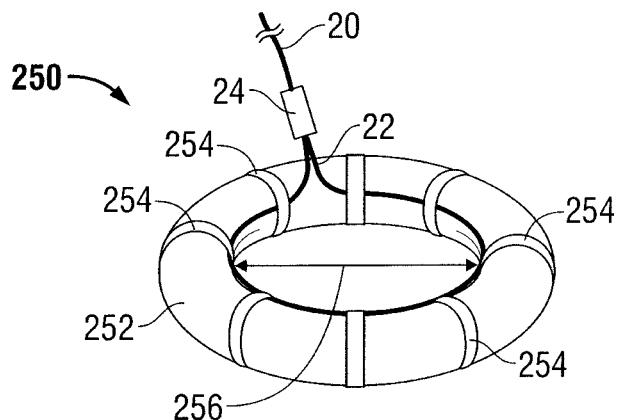
FIG. 15 is a perspective view of another embodiment of a fastening member for use with the anchor member of FIG. 7, wherein the fastening member is disposed in a first position.
Figure 16:
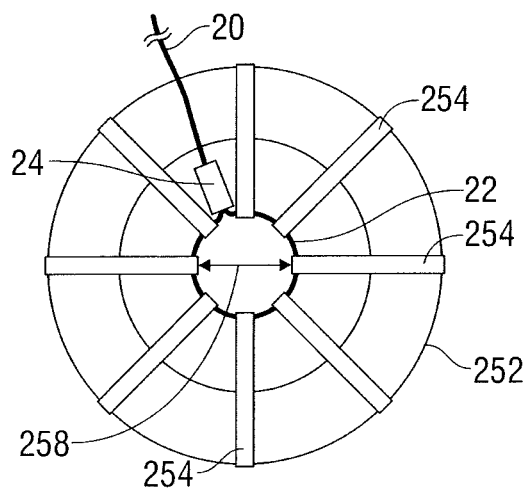
FIG. 16 is a top view of the fastening member of FIG. 15 shown in a second position.

Referring now to FIGS. 15-16, another embodiment of a fastening member according to the present disclosure is shown. Fastening member 250 includes a ring 252 having a plurality of elastic bands 254 spaced therearound. Ring 252 may be made from a rigid or a semi-rigid material, or a combination thereof. Suture 20 includes suture loop 22 that is disposed through the plurality of elastic bands 254. Cinch knot 24 is defined along suture 20 for selectively tightening suture loop 22. As shown in FIG. 15, when suture loop 22 is slacked, e.g., when cinch knot 24 is not tightened, elastic bands 252 retain suture loop 22 in close proximity to ring 252, defining opening 256 through suture loop 22. Fastening member 250 may pass over anchor member 30, with ball portion 32 and portion 406 of tissue 400 passing through opening 256 when in this slackened position. Once fastening member 250 is positioned adjacent shaft 33 (with tissue 400 therebetween), suture 20 may be pulled such that cinch knot 24 is slid therealong to tighten suture loop 22. As suture loop 22 is tightened, e.g., as the diameter of suture loop 22 is decreased, the converging suture loop 22 is moved away from ring 252 toward the center thereof, stretching elastic bands 254 in toward the center of ring 252. Suture loop 22 is sufficiently tightened to fixedly secure portion 406 of tissue 400 about shaft 33. In the tightened position, suture loop 22 is prevented from sliding along shaft 33 and from passing over ball portion 32 or base member 34. Thus, with tissue 400 and shaft 33 disposed through opening 258 and with suture loop 22 in the tightened position, portion 406 of tissue 400 is fixedly secured about anchor member 30.

Figure 17A:
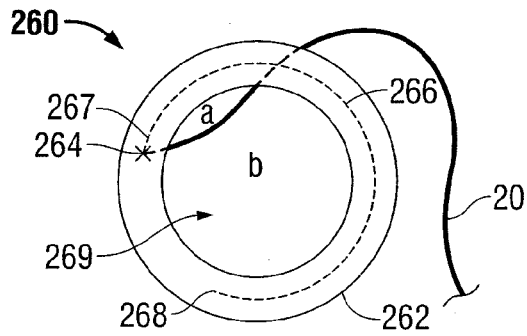
FIG. 17A is a top view of still another embodiment of a fastening member configured for use with the anchor member of FIG. 7, wherein the fastening member is disposed in a first position.

Another embodiment of a fastening member is shown in FIGS. 17A-17D, wherein fastening member 260 includes a ring 262 having a slot 266 including a first end 267 and a second end 268 defined therethrough. One end of suture 20 is attached to ring 262 at position 264 on ring 262. Suture 20 extends from position 264 through slot 266 of ring 262 and is moveable through slot 266 from the first end 267 to the second end 268 thereof. Suture 20 at least partially traverses the central bore 269 of ring 262, splitting central bore 269 into areas "a" and "b." As shown in FIG. 17A, when suture 20 is positioned close to first end 267 of slot 266, area "b" is much larger than area "a." Thus, ring 262 may pass over ball portion 32 of anchor member 30 (see FIG. 7), with ball portion 32 passing through area "b." Once ring 262 is positioned adjacent shaft 33, with portion 406 of tissue 400 disposed therebetween, suture 20 can be moved through slot 266.

Figure 17B:
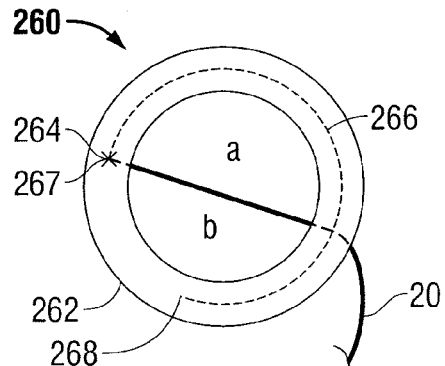
FIG. 17B is a top view of the fastening member of FIG. 17A shown transitioning between the first position and a second position.
Figure 17C:
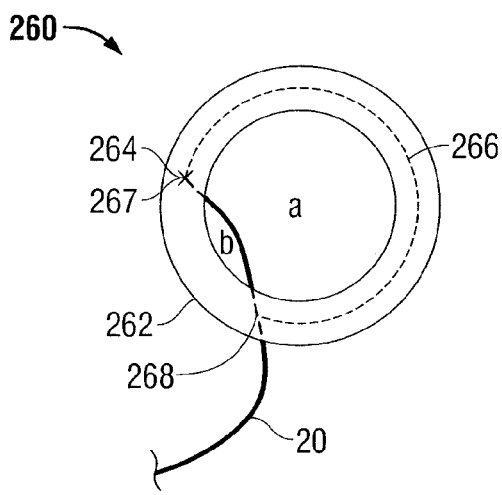
FIG. 17C is a top view of the fastening member of FIG. 17*b* shown in the second position.
Figure 17D:
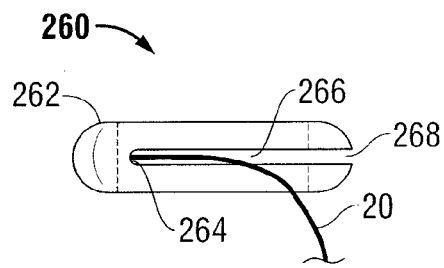
FIG. 17D is a side view of the fastening member of FIG. 17A.

As shown in FIG. 17B, as suture 20 is moved along slot 266, area "a" becomes larger while area "b" becomes smaller relative to area "a". Accordingly, suture 20 begins to cinch around shaft 33 of anchor member 30 as area "b" becomes sufficiently small. FIG. 17C shows the positioning of suture 20 at second end 268 of slot 266 wherein area "b" is much smaller than area "a." With anchor member 30 disposed through area "b," suture 20 may be fixed in slot 266 near second end 268 to fixedly retain portion 406 of tissue 400 around anchor member 30. Suture 20 may be secured via a clamping structure such as a jam cleat (not shown) positioned near second end 268 or may be secured by any other suitable clamping or other mechanical structure. Alternatively, suture 20 may be secured by engagement with one or more engagement means (not shown) e.g., hooks, tabs, slots, etc., formed integral to or connected to ring 262. As can be appreciated, securing suture 20 near second end 268 also secures fastening member 260 on shaft 33 of anchor member 30 wherein ball portion 32 and base portion 34 of anchor member 30 prevent sliding of fastening member 260.

An alternative embodiment of the tissue anchor applicator 10 described above and shown FIGS. 1-6 that is adapted for use with the fastening member shown in FIGS. 17A-17D (or any of the other fastening members described herein) will be described in greater detail below with reference to FIG. 22.

Figure 18A:
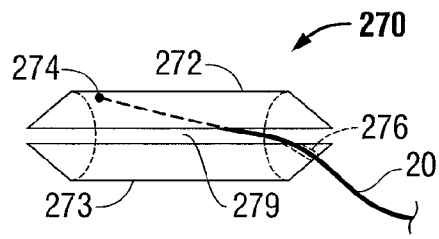
FIG. 18A is a side view of yet another embodiment of a fastening member for use with the anchor member of FIG. 7
Figure 18B:
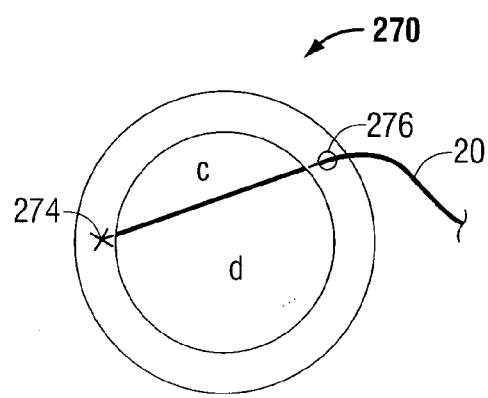
FIG. 18B is a top view of the fastening member of FIG. 18A.

Referring now to FIG. 18A-18B, wherein yet another embodiment of a fastening member is shown, a fastening member 270 includes stacked rings 272 and 273 and suture 20 affixed to ring 272 at position 274. Suture 20 extends from position 274 through aperture 276 defined within ring 273. As in the previous embodiment, suture 20 crosses the central bore 279 of rings 272 and 273, splitting central bore 279 into two areas, area "c" and "d." Ring 272 is fixed, while ring 273 is rotatable relative to ring 272. Alternatively, ring 273 may be fixed with ring 272 being rotatable or, in another embodiment, rings 272 and 273 may both be rotatable with respect to each other.

As suture 20 is pulled, ring 273 is rotated with respect to ring 272. As can be appreciated, upon rotation of ring 273 with respect to ring 272, area "c" is increased while area "d" is decreased. Thus, rings 272 and 273 of fastening member 270 may pass over ball portion 32 of anchor member 30 (see FIG. 7), with ball portion 32 passing through area "d" prior to pulling suture 20. Then, once fastening member 270 is positioned adjacent shaft 33, with portion 406 of tissue 400 disposed therebetween, suture 20 can be pulled, thereby rotating ring 273 and decreasing area "d." Upon further pulling and rotation, suture 20 cinches around shaft 33 of anchor member 30 as area "d" becomes sufficiently small or engagement means describe above. With anchor member 30 disposed through area "d," suture 20 may be secured via a clamping structure. Securing suture 20 secures fastening member 270 on the shaft 33 of anchor member 30 wherein ball portion 32 and base portion 34 prevent sliding of fastening member 270.

Figure 19A:
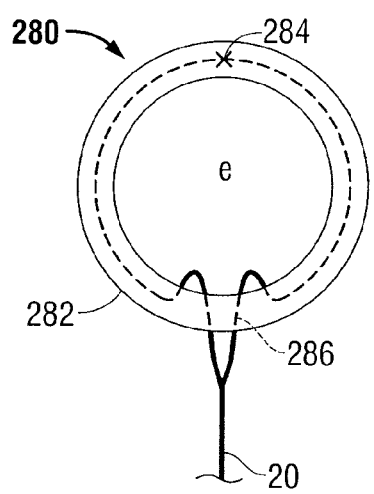
FIG. 19A is a top view of another embodiment of a fastening member for use with the anchor member of FIG. 7, wherein the fastening member is disposed in a first position.
Figure 19B:
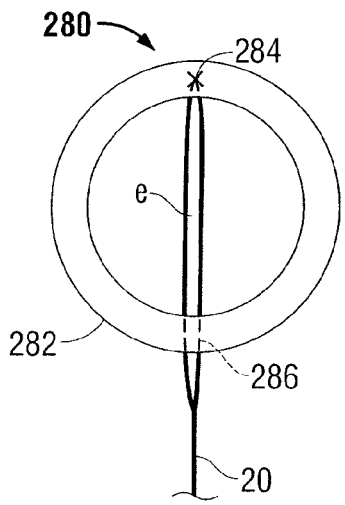
FIG. 19B is a top view of the fastening member of FIG. 19A shown in a second position.

Yet another embodiment, fastening member 280, illustrated in FIGS. 19A-19B includes ring 282 having a middle portion of suture 20 fixed thereon at position 284 wherein first and second ends of suture 20 are disposed through aperture 286 defined within ring 282. Suture 20 is moveable from a slack position (see FIG. 19A) to a taut position (see FIG. 19B) to cinch around portion 406 of tissue 400, thereby fixing portion 406 of tissue 400 around anchor member 30 (see FIG. 7). When suture 20 is slacked, area "e" defined therebetween is sufficiently large to allow passage therethrough of ball portion 32 of anchor member 30. When taut (FIG. 19B), area "e" is sufficiently small such that ball portion 32 and base portion 34 of anchor member 30 prevent sliding of fastening member 280 along the shaft 33, thereby retaining portion 406 of tissue 400 disposed around anchor member 30. Suture 20 thus conforms around shaft 33 of anchor 30 to fixedly retain portion 406 of tissue 400 around anchor member 30.

Figure 20A:
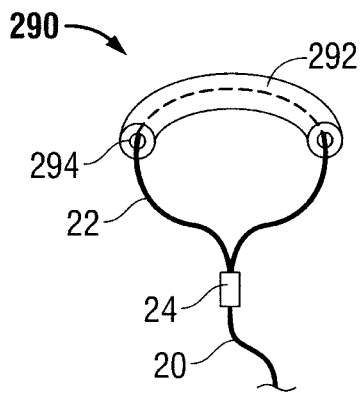
FIG. 20A is a perspective view of still yet another embodiment of a fastening member for use with the anchor member of FIG. 7, wherein the fastening member is disposed in a first position.
Figure 20B:
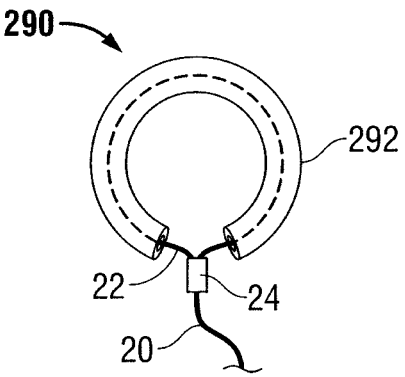
FIG. 20B is a top view of the fastening member of FIG. 20A shown in a second position.

Referring now to FIGS. 20A-20B, another embodiment of a fastening member 290 is shown including a suture 20 forming a suture loop 22 and having a cinch knot 24 configured to selectively tighten suture loop 22. Suture loop 22 is partially disposed through lumen 294 defined within tube segment 292. Tube segment 292 is dimensioned to create a minimum loop size of suture loop 22, as desired and as will be described below. As shown in FIG. 20A, tube segment 292 occupies a portion of suture loop 22 when suture loop 22 is in a slackened position. As suture loop 22 is tightened, tube segment 292 occupies more and more of the suture loop 22, ultimately reaching the position of FIG. 20B wherein tube segment 292 substantially surrounds suture loop 22. In other words, in the tightened position, as shown in FIG. 20B, tube segment 292 occupies the entire circumference of suture loop 22, preventing suture loop 22 from being tightened further. Accordingly, a specific length of tube segment 292 may be used to define a corresponding minimum loop size. When suture loop 22 is disposed about and cinched around tissue, tube segment 292 prevents the suture from being cinched too tightly, thereby preventing necrosis, ligation, or other similar damage to tissue.

It is envisioned that tube segment 292 may define varying lengths, depending on the diameter of tissue to be cinched, so long as tube segment 292 is short enough to allow suture loop 22 to fixedly cinch around tissue and so long as tube segment 292 is long enough to prevent damage to tissue as a result of over-tightening of suture loop 22. It is further envisioned that fastening member 290 be used in conjunction with anchor member 30, described in detail above (e.g., fastening member 290 may be cinched around shaft 33 of anchor member 30).

Figure 21A:
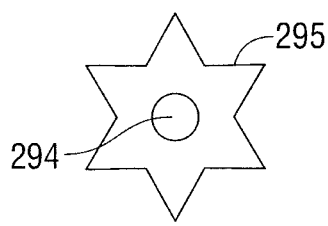
FIG. 21A is a transverse cross-sectional view of one embodiment of a tube portion of the fastening member of FIG. 20A.
Figure 21B:
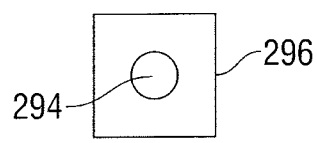
FIG. 21B is a transverse cross-sectional view of another embodiment of the tube portion of the fastening member of FIG. 20A.
Figure 21C:
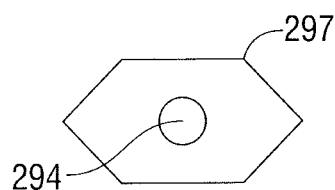
FIG. 21C is a transverse cross-sectional view of yet another embodiment of the tube portion of the fastening member of FIG. 20A.

FIGS. 21A-21C show different cross-sectional shapes for tube segment 292 which are configured help to increase the holding force of fastening member 290. Specifically, FIG. 21A shows tube segment 295 having a twelve-sided star, or dodecagonal shape: FIG. 21B shows tube segment 296 having a rectangular shape and FIG. 21C shows tube segment 297 having a hexagonal shape. Alternatively, tube segment 292 may have a circular, ovular, triangular, pentagonal, octagonal, or any other shape which helps increase the holding force of fastening member 290.

Figure 22:
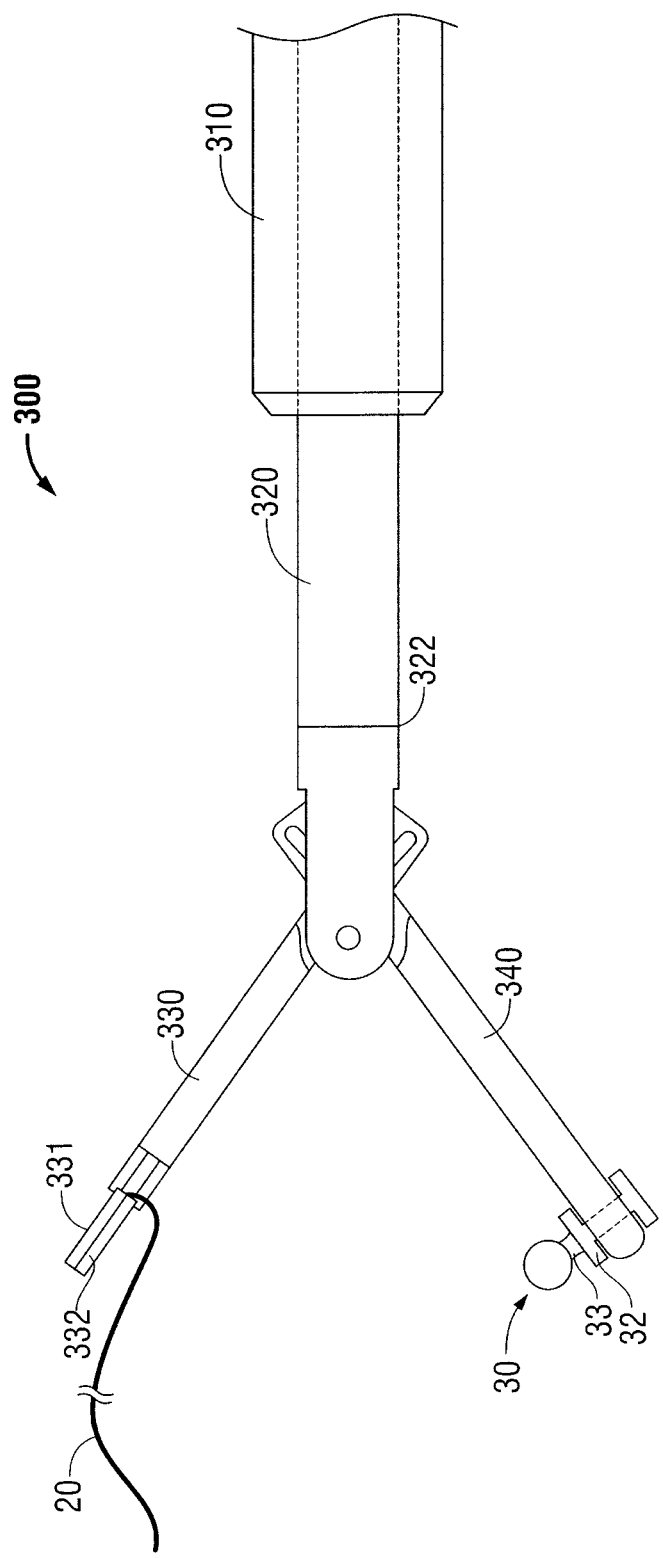
FIG. 22 is a side view of another embodiment of a tissue anchor applicator in accordance with the present disclosure.

With reference now to FIG. 22, another embodiment of a tissue anchor applicator is shown configured for use with, e.g., for applying to tissue, the tissue anchor assembly of FIG. 7 and/or any of the embodiments discussed above. The tissue anchor applicator is part of an end effector 322 of a surgical instrument 300. Surgical instrument 300 includes an outer tube 310 that is configured and adapted for a minimally invasive procedure (e.g., endoscopic or laparoscopic). A drive member 320 is slidably disposed within tube 310 for proximal and distal translation therein along a longitudinal axis of tube 310. End effector 322 is disposed at a distal end of drive member 320 and includes a pair of jaws 330, 340. Jaws 330, 340 are pivotably coupled to each other at a distal end of drive member 320 such that one or both of jaws 330, 340 is pivotable towards the other jaw, similar to jaw members 110, 120 of tissue anchor applicator 10 (see FIG. 1). It is contemplated that one jaw 330, 340 may be stationary while the opposing jaw 330, 340 is pivotable with respect to the stationary jaw 330, 340.

With continued reference to FIG. 22, drive member 320 includes a drive bar (not shown) disposed therein. The drive bar (not shown) is operably coupled to jaw members 330, 340 and is longitudinally translatable with respect to jaw members 330, 340 and drive member 320. The drive bar is coupled to jaw members 330, 340 such that longitudinal translation of the drive bar effects movement of jaw members 330, 340 between a spaced-apart position and an approximated position. More specifically, jaw members 330, 340 are moved from the spaced-apart position to the approximated position upon proximal translation of the drive bar. Distal translation of the drive bar, on the other hand, moves jaw members 330, 340 from the approximated position back to the spaced-apart position. Accordingly, surgical instrument 300 may further include an actuator, or trigger (not shown) coupled to the drive bar and configured for selectively translating the drive bar between a proximal position and a distal position. As such, the trigger may be selectively actuated to move jaw members 330, 340 between the spaced-apart and approximated positions.

In use, with continued reference to FIG. 22, anchor member 30, which was fully described hereinabove, is positioned on jaw 340. A fastening member includes a pair of rings 331, 332 extending distally from jaw 330. Rings 331, 332 include a length of suture 20 coupled thereto. It is envisioned that the fastening member be configured according to any of the embodiments of fastening member discussed above. It is also contemplated that jaws 330, 340 are releasably coupled to the distal end of drive member 320 using a releasable coupling. Suitable types of couplings (i.e., bayonet, etc.) are well known in the art. Alternatively, rings 331, 332 may be slidably coupled to jaw 330 and ball anchor 30 may be slidably coupled to jaw 340. In this arrangement, rings 331, 332 are separable from jaw 330 and ball anchor 30 is separable from jaw 340. Thus, in either embodiment, surgical instrument 300 may be disengaged from the tissue anchor and removed from the surgical site once the tissue anchor 30 has been applied.

As in previous embodiments discussed above with reference to FIGS. 1-6, tissue to be retracted is placed between jaws 330 and 340 when they are in the spaced-apart or un-approximated position, as shown in FIG. 22. Once the tissue is located between jaws 330, 340, the practitioner closes the jaws 330, 340, e.g., via actuating the trigger, thereby capturing tissue therebetween. More particularly, when jaws 330, 340 are closed or approximated, ball 32 of ball anchor 34 passes through the centers of rings 331, 332, urging tissue through rings 331, 332 as well. Thereafter, suture 20 may be pulled proximally to draw suture 20 snugly against tissue to fixedly secure tissue between suture 20 and shaft portion 33 of ball anchor 30. Thus, the tissue positioned between jaws 330 and 340 is releasably attached to ball anchor 30. Tissue may then be retracted in the same manner as in previously disclosed embodiments.

Once jaws 330, 340 are closed and tissue is secured using suture 20 and ball anchor 30, i.e., once anchor member 30 is fixedly engaged to tissue, drive member 320 is retracted such that rings 331, 332 and ball anchor 30 are separated, or released from jaws 330, 340 respectively. Tissue may then be retracted, held, or repositioned by manipulating suture 20, that is secured about tissue and ball anchor 30.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A tissue anchor applicator, comprising:
   an end effector assembly, the end effector assembly including:
      a first jaw member including a pair of spaced-apart arms releasably retaining a suture loop thereon; and
      a second jaw member releasably retaining an anchor member thereon, at least one of the first and second jaw members moveable with respect to the other from a spaced-apart position, wherein the suture loop and anchor member are spaced-apart relative to one another for positioning tissue therebetween, to an approximated position, wherein the anchor member extends at least partially though the suture loop for urging at least a portion of tissue through the suture loop, the suture loop selectively cinchable about the anchor member with tissue disposed therebetween for securing tissue about the anchor member to establish a tissue anchor when the first and second jaw members are moved to the approximated position, the tissue anchor maintained after release of the suture loop and the anchor member from the respective first and second jaw members.

2. The tissue anchor applicator according to claim 1, wherein, in the spaced-apart position, the tissue anchor is fixedly retained on the second jaw member.

3. The tissue anchor applicator according to claim 2, further comprising a locking mechanism, the locking mechanism retaining the tissue anchor on the second jaw member when the jaw members are disposed in the spaced-apart position.

4. The tissue anchor applicator according to claim 1, wherein, in the approximated position, the tissue anchor is released from the second jaw member.

5. The tissue anchor applicator according to claim 1, wherein at least one of the spaced-apart arms defines a pinch point between the arm and a distal end of the arm, the pinch point configured for releasably retaining a portion of the suture loop on the at least one arm.

6. The tissue anchor applicator according to claim 5, wherein applying a pre-determined pulling force to the portion of the suture loop releasably retained by the pinch point releases the suture loop from the arm.

7. The tissue anchor applicator according to claim 1, wherein the end effector assembly is disposed at a distal end of a shafted instrument including an actuator for moving the jaw members from the spaced-apart position to the approximated position.

* * * * *